(12) United States Patent
Faupel et al.

(10) Patent No.: US 7,615,354 B2
(45) Date of Patent: Nov. 10, 2009

(54) ELECTROPHORETIC SEPARATION OF COMPOUNDS

(75) Inventors: Michel D. Faupel, Eschentzwiller (FR); Hubert H. Girault, Ropraz (CH); Frederic Reymond, La Conversion (CH); Alexandra Ros, Werther (DE); Joel Stephane Rossier, Saillon (CH)

(73) Assignee: Ecole Polytechnique Federale de Lausanne, Lausanne (CH)

( * ) Notice: Subject to any disclaimer, the term of this patent is extended or adjusted under 35 U.S.C. 154(b) by 1353 days.

(21) Appl. No.: 10/275,041

(22) PCT Filed: May 4, 2001

(86) PCT No.: PCT/EP01/05704

§ 371 (c)(1),
(2), (4) Date: Oct. 30, 2002

(87) PCT Pub. No.: WO01/86279

PCT Pub. Date: Nov. 15, 2001

(65) Prior Publication Data

US 2003/0104449 A1 Jun. 5, 2003

(30) Foreign Application Priority Data

May 5, 2000 (GB) ................................. 0010957.9

(51) Int. Cl.
*G01N 33/53* (2006.01)
(52) U.S. Cl. ...................................................... 435/7.1
(58) Field of Classification Search ................ 435/7.1, 435/4, 285.2, 287.1, 287.7, 287.9, 288.4, 435/288.5, 288.6; 436/514, 518, 515; 422/58–61
See application file for complete search history.

(56) References Cited

U.S. PATENT DOCUMENTS

| | | | |
|---|---|---|---|
| 2,815,320 A | 12/1957 | Kollsman | |
| 3,719,580 A | 3/1973 | Roberts et al. | |
| 3,888,758 A | 6/1975 | Saeed | |
| 4,148,703 A | 4/1979 | Trop et al. | 204/180 G |
| 4,971,670 A * | 11/1990 | Faupel et al. | 204/459 |
| 5,104,512 A | 4/1992 | Gombocz et al. | |
| 5,126,022 A | 6/1992 | Soane et al. | |
| 5,149,418 A | 9/1992 | Flesher | |
| 5,540,826 A * | 7/1996 | Bier et al. | 204/610 |
| 5,773,645 A * | 6/1998 | Hochstrasser | 204/456 |
| 5,834,272 A | 11/1998 | Righetti | |
| 5,856,100 A | 1/1999 | Hayashizaki | |
| 6,007,865 A * | 12/1999 | Cerami et al. | 426/656 |
| 6,013,165 A * | 1/2000 | Wiktorowicz et al. | 204/456 |
| 6,328,869 B1 | 12/2001 | Ogle | |
| 6,638,408 B1 | 10/2003 | Speicher et al. | |
| 6,706,162 B1 * | 3/2004 | Voss et al. | 204/455 |

FOREIGN PATENT DOCUMENTS

| | | |
|---|---|---|
| DE | 2051715 | 4/1972 |
| EP | 0173081 A1 | 3/1986 |
| EP | 0 287 513 A2 | 10/1988 |
| EP | 0 323 948 A2 | 7/1989 |
| GB | 1422118 | 1/1976 |
| WO | 00/74850 A2 | 12/2000 |

OTHER PUBLICATIONS

Koegler et al., "Focusing Proteins in an Electric Field Gradient", *Journal of Chromatography A, Elsevier Science*, vol. 726, No. 1, pp. 229-236, Mar. 1996.
G. Kemp, "Capillary electrophoresis: a versatile family of analytical techniques", Biotechnol. Appl. Biochem, 1998, vol. 27, pp. 9-17.
Righetti et al., "Preparative protein purification in a multi-compartment electrolyser with Immoboline membranes", Journal of Chromatography, 1989, vol. 475, pp. 293-309.
Righetti et al., "Preparative electrophoresis with and without Immobilized pH Gradients", Advances in Electrophoresis, 1992, vol. 5, pp. 159-200.
Righetti et al., "Protein purification in multicompartment electrolysers with isoelectric membranes", Journal of Chromatography B, 1997, vol. 699, pp. 105-115.
Rylatt et al., "Electrophoretic transfer of proteins across polyacrylamide membranes", Journal of Chromatography A, 1999, vol. 865, pp. 145-153.
Zuo et al., "A method for global analysis of complex proteomes using sample prefabrication by solution Isoelectrofocusing prior to two-dimensional Electrophoresis", Analytical Biochemistry, 2000, vol. 284, pp. 266-278.

* cited by examiner

*Primary Examiner*—Ann Y Lam
(74) *Attorney, Agent, or Firm*—Howson & Howson LLP

(57) ABSTRACT

A device, method and kit for the electrophoretic separation and purification of charged and neutral compounds in an analyte solution. The device comprises a chamber (1), at least one wall of which is composed of a chemical buffering system (4). A potential difference is applied across the buffering system, resulting in the charged and neutral compounds being differentially separated by extraction of the charged compounds into the buffering system. The device also comprises means for collecting the separated compounds, preferably in ampholyte-free or buffer-free solution and optionally means for recycling the separated fractions.

40 Claims, 10 Drawing Sheets

A)

B)

ELECTROPHORETIC SEPARATION OF COMPOUNDS

TECHNICAL FIELD OF THE INVENTION

This invention relates to the electrophoretic separation, purification and recovery of compounds from solution.

BACKGROUND ART

Complex mixtures such as biological samples can contain up to 30,000 different proteins which need to be separated and identified for further analysis. In proteome analysis, high resolution separation of complex protein mixtures requires the development of novel techniques which minimize separation times, are easy to use, result in a high degree of purity and allow for further analysis of the compound(s) of interest extracted from the sample without unnecessary additional purification steps.

2D-gel electrophoresis is one technique which is capable of separating such complex biological samples (Wilkins, M. R. et al., Proteome Research: New Frontiers in Functional Genomics; Springer, 1997). With 2D-gel electrophoresis, proteins are separated first by an isoelectric focusing (IEF) step according to their isoelectric point. Secondly, proteins are separated as a function of their molecular mass by a polyacrylamide gel electrophoresis (PAGE) step. The result is a two-dimensional image in which each visible spot corresponds to a specific protein. If further analysis of a protein is required, for example, analysis of peptide composition or biological activity, then the protein has to be first extracted from the gel matrix before it can be analysed with the appropriate method to obtain the desired information.

Methods have been developed to extract proteins from a polyacrylamide 2D-gel, one such method consisting of cutting the gel around the protein spot and extracting it in a wet chemical step. With this technique there is a high probability that the protein will be denatured, modified or even lost during its retrieval. Another technique is electroblotting, which is very time-consuming.

Once a protein is extracted from the gel, the most powerful analytical technique is mass spectrometry. Using this technique, it is not only possible to analyse the peptide composition of proteins, but also to compare the obtained peptide map to other protein data compiled in data banks by several bioinformatical institutions. In mass spectroscopy (MS), the purity of a sample is critical. If a sample contains impurities such as salt, this is not directly amenable to MS analysis. Such a sample would require desalting before MS analysis by means such as a dialysis procedure. Another way of avoiding undesired compounds in the sample is to use a direct laser desorption technique from the 2D-gel (Ogorzalek Loo R. R., et al., Analytical Chemistry, 1996, 68, 1910-1917) or an electroblotted 2D-gel (Eckerskom, C. et.al., Analytical Chemistry, 1997, 69, 2888-2892; Strupat, K. et al. Analytical Chemistry, 1994, 66, 464-470). All of these additional purification steps complicate the analysis procedure and are time-consuming.

While separation of compounds in complex mixtures is possible with 2D-gel electrophoresis, there persists the problem of the numerous impurities which remain together with the compounds desired for analysis, removal of which is laborious. The major problem with 2D gel-electrophoresis is that the compound of interest is trapped within a gel and must be extracted and further purified before it can be analysed.

Another method of separating complex biological samples is by isoelectric separation for example by iso-electric focusing (IEF) (Righetti, P. G., J. Biochem Biophys Methods, 1988 16:99-108). IEF is a technique of electrophoresis whereby compounds can be separated on the basis of charge within a pH gradient. In general, there are two major types of isoelectric focusing systems: (i) free flowing buffered systems and (ii) immobilised buffered systems.

(i) Free Flowing Buffering Systems

All free flowing systems are based on the use of a buffer, usually carrier ampholytes or isoelectric buffers such as amino acids. For example, a continuous free flow device has been demonstrated by Soulet, N. et al. (Electrophoresis, 1998, 19, 1294-1299). In this device, a pH gradient is created in a flat chamber using carrier ampholytes and a potential gradient perpendicular to the carrier flow direction. The sample is continuously injected and partitioned at the end of the device in discrete fractions. Although the pH gradient was stable over several hours, a complete separation of bovine serum albumin and alpha-lactalbumin could not be achieved. Some major drawbacks of this system are that it is not able to separate compounds which have close pI values, that it takes several hours for the separation to occur and that it also uses carrier ampholytes which need to be removed before further analysis of the desired compounds is possible.

In isoelectric split-flow thin (SPLITT) fractionation, no pH gradient is established, but the separation principle is based on the charge that proteins exhibit depending on their isoelectric point (pI) in buffers of different pH. A potential is applied to a flow cell using adequate outlet and/or inlet splitters to separate the protein fractions. Two component protein mixtures have been successfully separated (Fuh, C. B. and Giddings, J. C., Separation Science and Technology, 1997, 32, 2945-2967), but this system exhibits some drawbacks when complex protein samples have to be analysed and when the isoelectric points (PI) of proteins are very close (pI differences less than 0.1 pH unit are not possible to separate using this method).

Many recycling isoelectric systems are based on the physical separation of compartments with different pH by means of membranes or screens. Some of them have been reviewed in the literature (Bier, M. Electrophoresis, 1998,19,1057-1063; Krivankova, L. et al., Electrophoresis, 1998, 19, 1064-1074). One of the most common preparative approaches to recycling free-flow electrophoresis is the Rotofor apparatus, commercialised by BioRad. In a tube-like apparatus where compartments are defined by a screening material, the pH gradient is established using special ampholytes, the so-called Rotolytes. Gravity problems in free flow electrophoresis are overcome by the rotation of the separation compartments. This device has been successfully applied to the preparative scale. A modification of this approach is the tangential electrophoretic apparatus from Bier, (U.S. Pat. No. 5,540,826). Here, the different compartments are arranged in such a manner that an array of multi-channels is separated from a second array of multi-channels slightly displaced through a single screen. An electrical field is applied perpendicularly to the channels which enables an electrophoretic serpentine pathway through the channels. The pH in the channels is fixed by ampholytes and recycling is possible with independent inlet and outlet ports at every channel. The major disadvantages of this system are that the device has a complicated construction of multi-channels through which the solution must flow and that the compound(s) of interest remain(s) in an ampholyte solution which needs to be removed before further analysis of the desired compound or compounds is possible.

In most solution-buffered systems, the analyte is mixed with a running buffer and several strategies of fluid handling are presented to either fractionate or desalt the sample or to work in a non convective and/or low water diffusion medium. All these isoelectric focusing devices have a major disadvantage in terms of further analysis of compounds. They all contain in the final separated fraction a certain amount of undesired buffering species or ampholytes.

(ii) Immobilized Buffering System

In most immobilized buffering systems, there is a major disadvantage in terms of further analysis of compounds since the final separated fraction is trapped in a gel or membrane.

There is a device developed by Righetti and Faupel (Righetti, P. G. et al. Journal of Chromatography, 1989, 475, 293-309) which is based on a technique known as "segmented immobilized pH gradients". The device is composed of multiple compartments sandwiched between an anodic and a cathodic reservoir separated by immobiline isoelectric membranes, allowing the recovery of proteins in an ampholyte-free solution. This device can be composed of several compartments separated by immobiline gels stabilised by membranes. The separation of fractions is achieved in such a way that the protein stops migrating in an electrical field in between two immobiline membranes, wherein one membrane establishes a pH higher than the protein's pI and the other a pH lower than it. There are several disadvantages of this apparatus: the use of multiple compartments, multiple immobilized membranes and segmented pH gradients.

SUMMARY OF THE INVENTION

The invention seeks to provide a device, method and kit for separating charged and neutral compounds and for the recovery of said neutral compounds in a solution which can be an ampholyte-free or a buffer-free solution. There exists a need in the art for a device, method and kit for separation of compounds in complex mixtures combined with an efficient method of recovery of compounds of interest in order that they may be further analysed, for example by mass spectrometry, without additional time-consuming steps of extraction and purification which exist in the prior art. The invention described herein can be used to separate biological or chemical compounds within complex mixtures.

In one aspect, the present invention provides a device for electrophoretic separation and purification of charged and neutral compounds in an analyte solution, said device comprising: (a) a chamber, at least one portion of a wall of the chamber being composed of a chemical buffering system; (b) a means for producing an potential difference across said chemical buffering system whereby said charged and neutral compounds may be differentially separated by extraction of said charged compounds into said chemical buffering system; (c) a means for collecting separated fractions, if desired in solution such as an ampholyte-free or buffer-free solution and (d) optionally, means to recycle separated fractions.

In another aspect, the present invention provides a method of electrophoretic separation and purification of charged and neutral compounds in an analyte solution and collection of separated fractions using the device of the present invention. A further advantage of the present invention is that compounds of interest are recoverable in solution, even in ampholyte-free or buffer-free solution.

The present invention relates to a method of separation and purification which is fundamentally different from the prior art electrophoresis techniques, since the potential difference is not applied in the analyte solution nor between the analyte solution and the chemical buffering system. In the present invention, the potential difference is only applied through the chemical buffering system (or a portion thereof), in such a manner that a portion of the electric field penetrates the chamber containing the solution to purify. This novel method and apparatus thereof has the advantage over prior art methods to increase the resolution of the separation, to accelerate the purification speed due to the migration in solution instead of in a gel or a membrane and to allow for direct fractionation for further analysis. It is not necessary to use additional purification steps used in other prior art electrophoretic devices and methods which use carrier ampholytes or isoelectric buffers that are commonly used to create a pH gradient in the analyte solution.

In the present invention, the chemical buffering system may be advantageously controlled with respect to the pH in its portion contacting the analyte solution. When the compound or compounds of interest are globally neutral at the controlled pH, one is able to separate the desired compound or compounds of interest from the mixture. Upon application of an electric field through the chemical buffering system, preferably perpendicular to the analyte solution, it is possible to discriminate between charged compounds and compounds that are globally neutral at this pH. Indeed, the neutral compounds in contact with the buffering system are maintained in the analyte solution, whereas the charged compounds migrate into the chemical buffering system. In this manner, compounds may be separated by pI by controlling the pH of the chemical buffering system.

The present invention therefore permits the electrophoretic separation and purification of compounds that are globally neutral from charged species directly in an analyte solution which does not need to be buffered. In some embodiments of this invention, the device has a chamber having an inlet and outlet connected to a hydraulic flow system, wherein the analyte solution is capable of flowing through said chamber. In other embodiments, the device has a chamber in which the inlet and outlet are merged, thereby constituting a simple reservoir in which the mixture to purify can be deposited and from which the purified solution can be retrieved. In further embodiments, devices according to the invention may contain a plurality of chambers for simultaneous and/or parallel purification. Preferably, the direction of the electrical current is perpendicular to the direction of the flow of the analyte solution.

In preferred embodiments, the chemical buffering system has a defined pH value or a defined pH range, which may be achieved, for example, by using covalently linked buffering molecules, amphoteric isoelectric membranes, or any combination thereof. The chemical buffering system is therefore capable of separating the compound of interest by isoelectric point at a fixed pH or in a pH gradient. It is capable of separating compounds with different pI, for example compounds with differences in pI less than 0.1, compounds with differences in pI less than 0.01 and compounds with differences in pI of up to 0.001, thereby permitting different desired degrees of purification.

The chemical buffering system can be, for example, an immobiline gel, a fluid solidified in a polymer matrix, a fritted glass, a porous membrane, a filter or any combination thereof. This chemical buffering system serves to control the pH in its portion contacting the analyte solution, thereby allowing discrimination between charged compounds and compounds that are globally neutral at this pH. Said chemical buffering system can thus be used to separate one or several neutral compounds of interest from a mixture containing charged compounds.

An electric current is applied across said chemical buffering system, and the shape of the chamber is designed in such a manner that the electric current penetrates within this chamber, thereby generating a migration flux of the charged compounds present in solution. The purification efficiency and rate depend on the depth, on the width and length or on the diameter of the chamber, and its geometrical shape can thus be chosen with respect to the purpose of the applications and experiments to be carried out.

One advantage of the present invention is that the separation induced by the migration of charged compounds allows the compound of interest to be fractionated directly within the analyte solution. In this manner, the separation is much faster than in prior art methods since the rate of migration is much faster in solution than in other kinds of media commonly used in the prior art such as gels or porous membranes where the high resistance drastically decreases the migration speed.

In some cases, the migrating charged molecules can penetrate into the chemical buffering system and further migrate within it. However, this migration does not affect the separation within the analyte solution, and the chemical buffering system can be regarded as a waste reservoir. In some applications, it can be advantageous to prevent the adsorption of the neutral compounds onto the wall of the chemical buffering system. In some embodiments of the present invention, means may be provided to stop direct absorption, comprising, for example, a fine membrane, which can be (for instance) a material of very low porosity.

In some instances, it can also be advantageous to recover the charged molecules that migrate within the chemical buffering system. To this end, the device of the present invention may advantageously contain a plurality of sub-chambers.

In some embodiments of the present invention, an analyte solution can be caused to flow from an inlet an to outlet within the chamber. Computer simulation experiments show that the electric field applied through the chemical buffering system penetrates into the flow chamber, which provokes the migration of the charged species in the analyte solution (see examples). The computer simulation demonstrates that if the electric field is directly applied between the extremities of the chamber containing the analyte solution, only a very small portion of the current lines penetrate into the chemical buffering system, forcing the charged species to migrate within the analyte solution. This mode of polarisation has been used in prior art methods (as in segmented gel electrophoresis), but to avoid these imperfections, the current within the chemical buffering system is increased by polarising the solution in such a way that the ions are forced across the chemical buffering system which is then used as a septum or a filter separating a network of solution compartments. In contrast to the prior art, the present invention embodies a separation principle fundamentally different since the potential difference is applied at both extremities of the chemical buffering system in such a manner that a portion of the electric field penetrates the chamber containing the solution to purify.

The present invention has the advantage that a single chamber is sufficient to perform the necessary separation, although a plurality of chambers (or sub-chambers) can be used, if desired, in order to perform simultaneous separations at various desired pHs or parallel separations at the same desired pH in the chemical buffering system. Furthermore, there is no limitation to the number, dimensions or shape of the chambers, which can be adapted to the specific required application without restriction of size, volume or quantity. Therefore, the devices and methods of the invention can readily be scaled up or down. For example, it is possible to operate an analysis level, as well as at preparative and pilot scales or in down stream processes.

In some embodiments, the devices of the present invention may have means to control the temperature of the device and the analyte solution, particularly where high potential differences are employed.

In some preferred embodiments, devices according to the present invention may be provided with means to prevent precipitation of the neutral compound(s) of interest. Upon purification, the analyte solution becomes impoverished in ions, thereby decreasing its solubility. In such circumstances, the use of non-aqueous analyte solution or the integration of a sonicator in the device of the present invention may be advantageous.

In operation of devices according to the present invention, all compounds that are charged at the pH established by the chemical buffering system migrate towards the extremities of the chamber, following the lines of current which depend on the position of the electrodes, on the geometry of the whole device and on the nature of both the analyte solution and the chemical buffering system. In the analyte solution remain only the compounds that are neutral at the pH defined by the chemical buffering system.

The present invention permits rapid elimination of all undesired ions, including salts, charged acids or bases, buffer components or ampholytes from a solution. For instance, proteins can be purified in free flowing solution and simultaneously prepared for further analysis. Similarly, the present invention can be used to isolate a neutral compound from excess charged by-products or salts.

In addition to the isolation of neutral species, the devices and methods of the present invention also facilitate the extraction of charged species, which, in operation, are loaded into the chemical buffering system. For example, one important issue in proteome analysis is to have access to low abundant proteins, the identification of which is often hampered by the presence of highly concentrated ones. For instance, the presence of albumin in many cellular extracts prevents the detection of proteins which are present in low concentration. In such applications, the present invention can for instance be used to separate albumin from the rest of the analyte solution by loading in an immobilised pH gradient (IPG) gel. To this end, the portion of the chemical buffering system in contact with the analyte solution must have a pH range encompassing that of albumin or of any other compound that needs to be separated from the rest of the analyte solution. In this manner, all the compounds of the analyte solution that are charged in this pH range are extracted upon application of the electrical field into the IPG gel and are liable to migrate within this gel as long as they remain charged or up to the point where the pH of the gel corresponds to their respective pI. In such cases, the compounds of interest are not only the neutral compound(s) remaining in the analyte solution after electrophoretic purification, but also—and sometimes mainly—the charged compounds that have been extracted and that have migrated within the chemical buffering system, since the latter are amenable to better determination and identification than in the prior art.

In one mode of use, the present invention can be used to accumulate compounds in the chemical buffering system. In such applications, the analyte solution is renewed in the chamber, in such a manner that fresh solution is submitted to electrophoretic separation and purification. In this manner, compounds of low concentration in the analyte solution can be accumulated in the chemical buffering system, thereby facilitating their detection and identification. For identification purposes, it can also be advantageous that the chemical buffering system be associated with means to specifically identify a compound or a class of compounds. Such means may operate to detect a compound or a class of compounds by for instance emission of light, absorption of light (as in blotting), generation of an electroactive product, specific molecular recognition (for example as in the formation of an antigen-antibody complex or in an enzymatic reaction) that generates a detectable product.

In some embodiments, the device may be modified to facilitate the recovery of charged compounds that have been extracted from the analyte solution into the chemical buffering system. To this aim, the chamber may be divided into subchambers, at least one of them containing the analyte solution. The other subchambers may be used for collecting the compounds that migrate within the chemical buffering system and preferably contain a buffer solution to fix the pH. As the charged compounds migrate along the direction of the electrical field and as a portion of this electrical field penetrates into each subchamber the charged compounds can be extracted back from the chemical buffering system into the subchambers. This migration continues until the migrating compounds reach a pH region of the chemical buffering system or a subchamber where they are globally neutral. Such a configuration illustrates another advantage of the present invention, namely that it permits the recovery of any compound in solution, even after migration within the chemical buffering system. This is of great advantage with respect to the prior art, because it greatly facilitates further analysis of such recovered compounds.

The devices and methods according to the present invention have at least the following major advantages: (i) high sample recovery of compounds of interest directly in solution (ii) a high resolving power depending on the pH interval across the isoelectric point (pI) of the desired compound (iii) a rapid separation rate due to the charged molecules migrating in solution rather than through denser materials such as gels and (iv) separation of the desired compound of interest occurs directly into a ampholyte-free or buffer-free solution which conveniently facilitates further analysis without the need for extensive additional purification steps, such as desalting.

The compound or compounds of interest are preferably biological compounds, more preferably organic compounds, and most preferably, proteins, protein derivatives, protein isoforms, enzymes, antigenes, antibodies, peptides or nucleic acids, lipids or carbohydrates.

In a yet further aspect, the invention provides a kit comprising the device of the present invention with instructions for the electrophoretic separation and purification of charged and neutral compounds in an analyte solution and, optionally, with the chemicals to mix or to use with the analyte solution to improve the purification of the desired compound(s). Such a kit permits the compound or compounds of interest to be recoverable in solution.

The compound of interest may be any biological or chemical compound which is neutral at the pH or in the pH interval defined by the chemical buffering system in contact with the analyte solution. Preferably, the compound of interest is an ionisable biological compound such as a protein, an enzyme, a peptide or a compound containing a peptide or protein moiety such as a glycoprotein, but can also be a nucleic acid, complex lipid or complex carbohydrate. It can also be any of various isoforms of a protein or an antibody such as a monoclonal antibody.

The charged compound may be any compound that is charged at the pH or in the pH interval defined by the chemical buffering system in contact with the analyte solution. The charged compound can thus be either a ionisable or charged compound, preferably an acid, a base, an ampholyte or a permanently charged compound like for example a dissociated salt. The charged compound is extracted from the chamber into the chemical buffering system upon electrophoretic separation according to the present invention. It can yet be further extracted out of the gel into a solution and may the compound of interest for the experimenter.

The analyte solution may be any solution according to the present invention which solubilizes the desired compound(s) of interest. It is preferably an ampholyte-free or buffer-free solution.

The electric current can be applied by means of electrodes generated by an external power supply. Any voltage the device of the present invention can tolerate may be used (e.g. 10 to 10000 volts, preferably 100 to 5000 volts). Higher voltages may be used provided that the generated heat can be dissipated by proper cooling. Additionally, the voltage can be programmed to enable the application of any voltage waveform, including alternative current and square wave.

The chamber is not limited in the number of subchambers, dimensions or shapes, which can be varied as required by the specific application of the device. The chamber may also be used as a module in conjunction with other separation, purification or detection components. The parts comprising the chamber may be machined from solid plastic such as plexiglass, moulded out of a thermoplastic resin, or made by any other suitable manufacturing process. The material should have chemical resistance to the analyte solution, the electric current, weak acids and bases, oxidants and so forth. In addition, it may be desirable to have optical clarity or at least some degree of transparency. The chamber may be supported by an electrical insulating substrate made by an electrical insulating material such as a porous membrane, a porous mineral layer, a non-conductive polymer (such as for example plexiglas) or a network of electrical insulating fibres. The chamber may also have a means to ensure proper fit and positioning of the components in the chamber such as, for example, the use of an O-ring to ensure that the chamber is flow tight to prevent leakage of the analyte solution, or, for example, screws to fasten the walls of the device together. Furthermore, the chamber is made of any material able to support voltages, like for example plexiglass.

The chemical buffering system may be any system by which the separation of charged compounds from the compound(s) of interest can be facilitated. For example, the chemical buffering system can be a gel, most preferably an immobiline gel, a fluid solidified in a polymer matrix, a fritted glass, a porous membrane, a filter or any combination thereof. The chemical buffering system can also have a means to stop direct penetration of charged and neutral compounds in said chamber such as low adsorption material. The chemical buffering system is most preferably thin, free of electroosmosis and flow-tight.

The pH can be a fixed pH or a pH gradient. For example, it can be produced using covalently linked buffering molecules, such as for example thiomorpholine derivatives or acrylamide derivatives. The gradients of pH can be made by amphoteric isoelectric immobilized pH-membranes, said membranes may have very short pH-gradients covering only a very narrow pH-interval. Ideally, said pH-interval can reach the ultimate pH of the compound of interest to be separated and purified. With the method of the present invention, it may be possible to separate compounds with pI difference up to a maximum resolution of pI to 0.001.

The hydraulic flow may be generated by means such as pressure, aspiration, centrifugal forces or electrical means. The direction of the hydraulic flow is at any suitable angle, most preferably perpendicular, with respect to the direction of the electrical current. The flow can be in single pass or recycled by means of fluid recycling loops. Furthermore, the flow can be distributed in a plurality of chambers, one extremity of which can be interconnected to a single inlet or outlet. Other components may be included in the external flow channels, such as heat exchangers, reservoirs extending the volume capacity of each recirculating loop, and sensors such as for example a pH sensor a temperature sensor and/or a light absorption sensor.

The invention is hereinafter described in more detail by way of example only, with reference to the attached figures which are briefly described below.

A) I: Potential distribution in the device when σ(gel)=σ(solution)

II: Current vectors when σ(gel)=σ(solution)

B) III: Potential distribution in the device when 10σ(gel)=σ(solution)

IV: Current vectors when 10σ(gel)=σ(solution)

Figure 3:
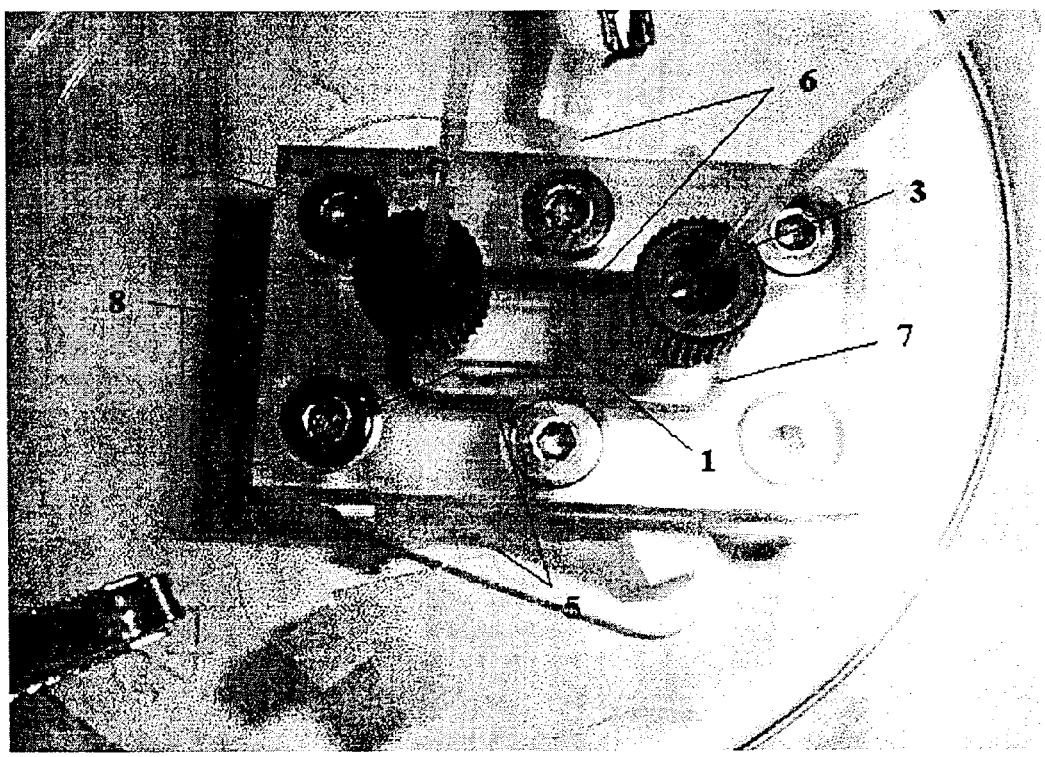

FIG. 3. Photograph of a prototype of separation device showing an arrangement similar to that represented in FIG. 1. The chamber 1 possesses one inlet 2 and one outlet 3 that are connected to tubings to permit analyte solution flow through the device. The chemical buffering system 4 is an immobilised pH gradient (IPG) gel placed above the chamber. The entire device is held in a screwed Plexiglas support 8, and its integrity is ensured by an o-ring 7 which allows a tight seal. The cathode 5 and the anode 6 are placed in contact only with the IPG gel, close to the o-ring. These electrodes are made of a thin platinum wires, so that they can go above the o-ring without generating any leakage in the device. When the gel reswells in the device, it encloses the electrodes completely and prevents the analyte solution from touching the electrodes.

Figure 4:
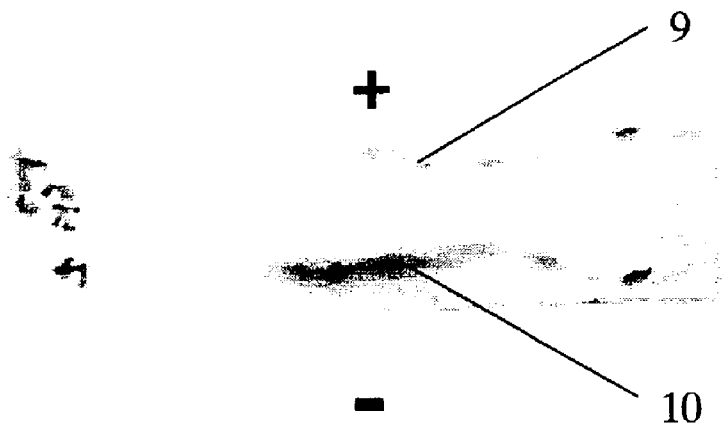
Figure 4:
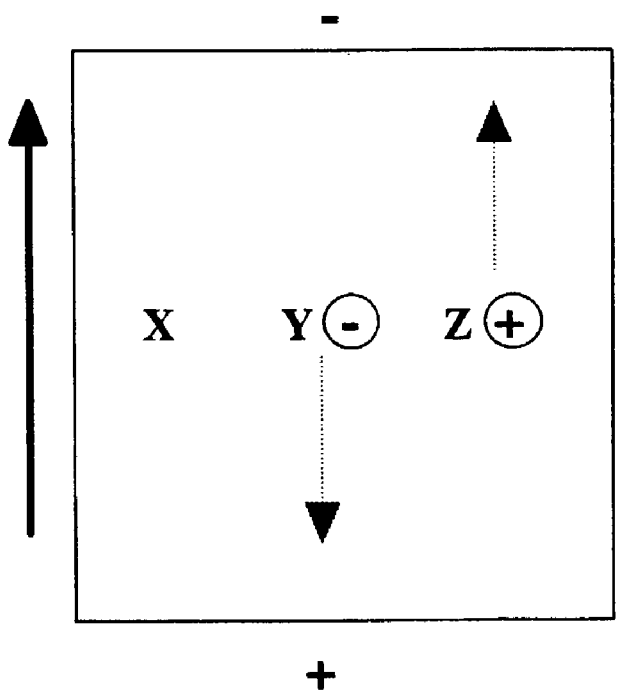

FIG. 4. A) Photograph of an immobiline gel at pH=7±0.14 pH units after purification in the separation device of FIG. 3 of a solution of IEF markers in water upon application of an electrical field of 100 V during 1 hour. The migration of the negatively charged protein phycocyanin (band 9) to the anode and of the positively charged proteins like cytochrome c, myoglobin and haemoglobin (band 10) to the cathode is visible by eye in this experiment. B) schematic diagram showing the separation process in the immobilised pH gradient gel. The arrow indicates the direction of the pH gradient (low pH value at the anodic side of the gel and high pH value at the cathodic side of the gel). During the separation, a compound X with a pI corresponding to the pH of the portion of the gel in contact with the analyte solution is globally neutral and does not migrate. A compound Y with a pI(Y)>pI((X) is negatively charged in this pH range and migrates toward the anode, whereas a compound Z with pI(Z)<pI(X) is positively charged in this pH range and migrates toward the cathode. The dotted arrows indicate the direction of the migration of these various compounds.

Figure 5:
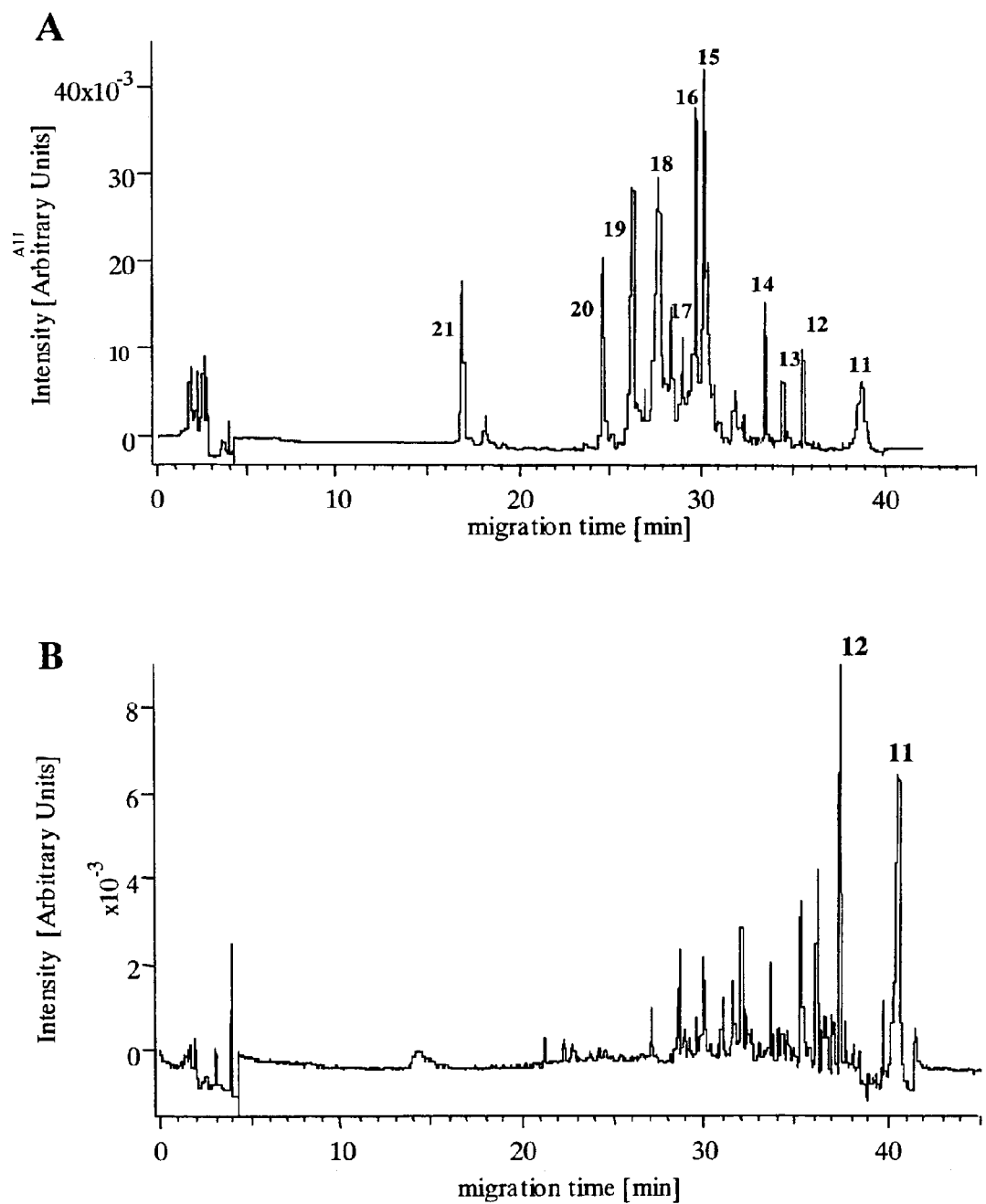

FIG. 5. Purification experiment using a segment from pH 4-5.5 from an immobiline DryPlate.

A) Electropherogram obtained from CIEF analysis of IEF standards as applied for the experiment. Peaks 11 to 21 corresponds to the proteins of Table 1 below C) Electropherogram of the solution obtained after the experiment, showing that only peaks 11 and 12 remain of large intensity after purification.

Figure 6:
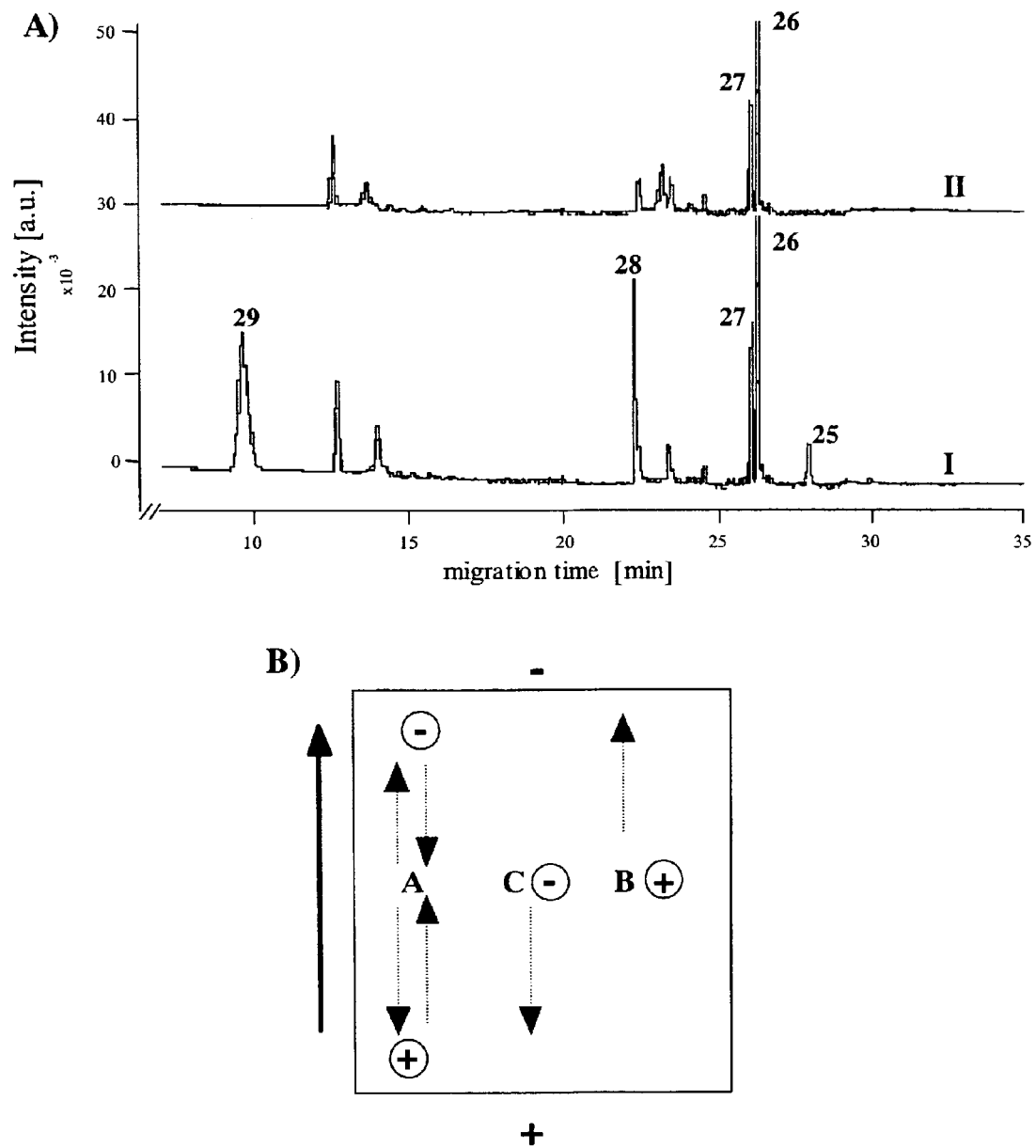

FIG. 6. Purification of a mixture containing 5 different proteins, namely: trypsin inhibitor (pI=4.6, peak number 25), β-lactoglobuline B (pI=5.2, peak number 26), β-lactoglobuline A (pI=5.3, peak number 27), equine myoglobine (pI=7.0, peak number 28) and equine cytochrome c (pI=9.6, peak number 29).

A) CIEF analysis of: I) the applied protein mixture to purify; II) the protein solution after the separation experiment with an immobiline section of a pH range between 5.06 to 5.34.

B) Scheme for the separation principle of the present experiment in a separation device when using an immobiline gel with a pH gradient. The protein of interest (noted A in the scheme) has a pI in between the extremes of the pH gradient, i.e. between pH 5 and 5.4 in the present case. Proteins symbolised by B and C in the scheme have a pI larger than 5.4 or, respectively, smaller than 5.0, so that they are positively and, respectively, negatively charged in the immobilised pH gradient gel. The dotted arrows show the direction of the migration of these various proteins, whereas the solid arrow shows the direction of the pH gradient between the anodic and the cathodic extremities of the gel (noted by a positive and, respectively a negative sign). Upon application of the electric field, proteins of types B and C migrate into the immobiline gel and are thus separated from the proteins of type A.

Figure 7:
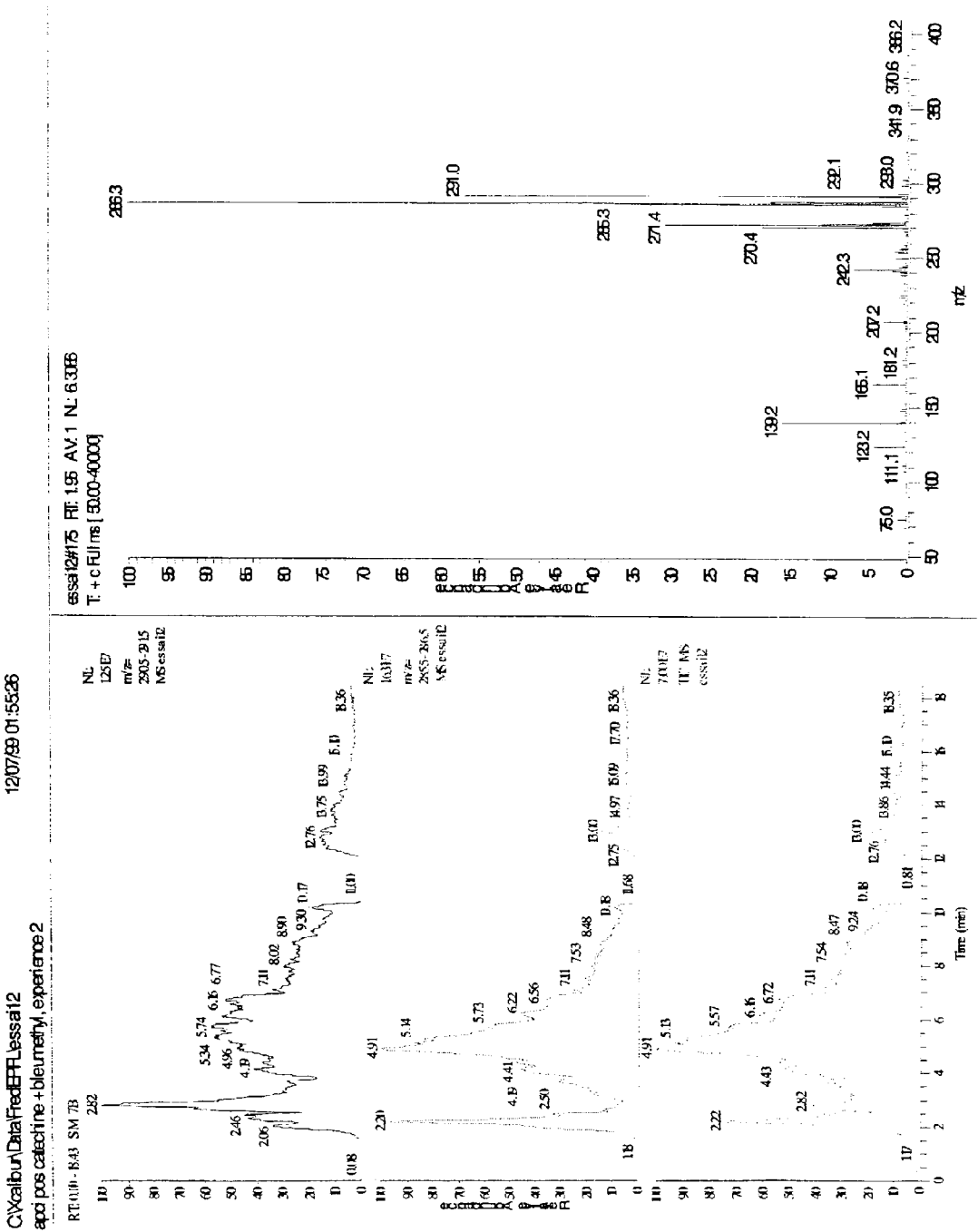

FIG. 7. Mass spectrum (on the right side of the figure) obtained by single syringe injection of 2 μL of a solution of 80 μM catechine and 20 μM methylene blue, including (on the left side of the figure) the evolution with time of the relative abundance of the peaks of mass 290.5-291.5 (upper graph), of the peak of mass 285.5-286.5 (middle graph) and of the total abundance of these two peaks (bottom graph).

Figure 8:
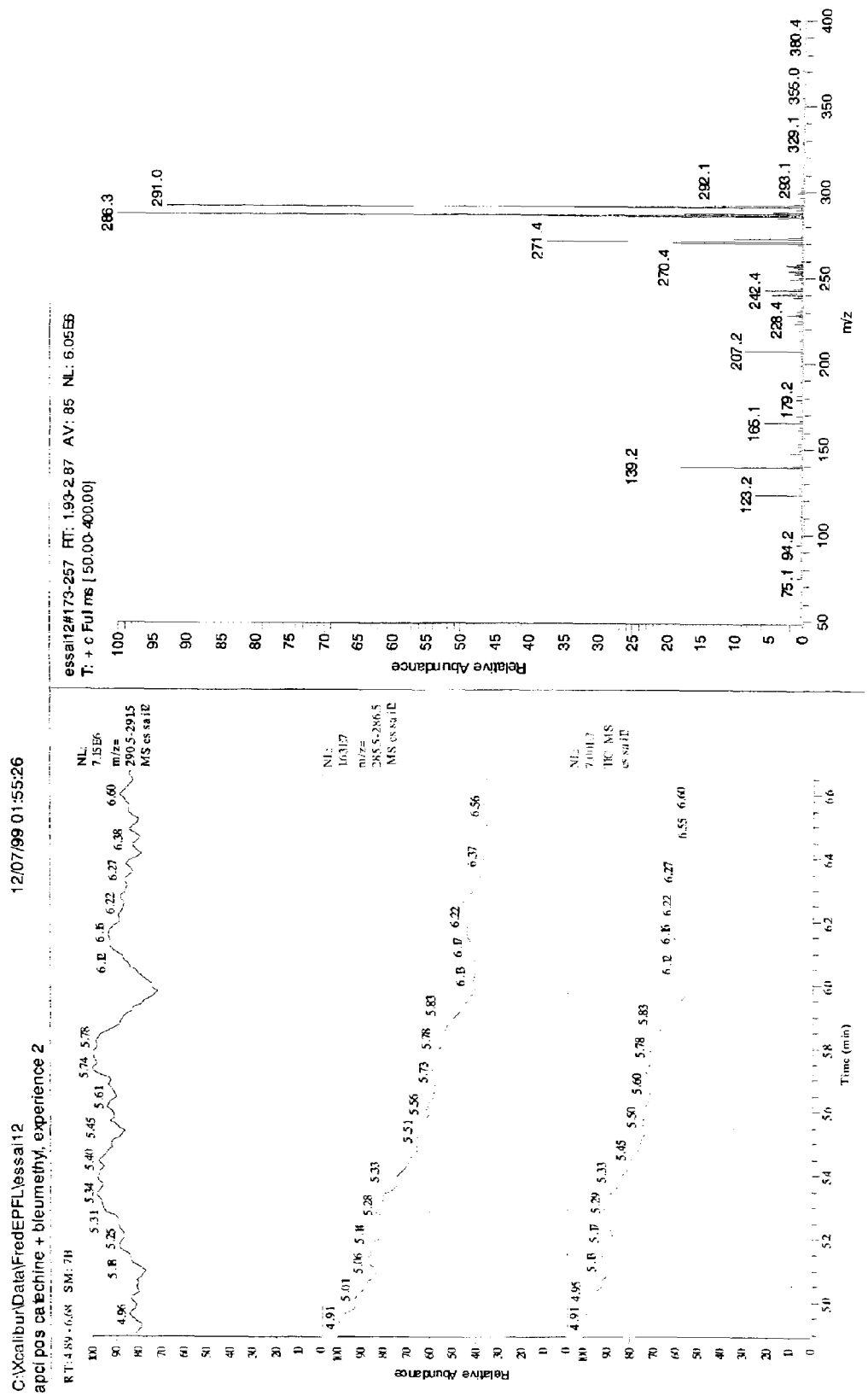

FIG. 8. Mass spectrum (on the right side of the figure) obtained by continuous injection of a purified solution of 80 μM catechine and 20 μM methylene blue, including (on the left side of the figure) the evolution with time of the relative abundance of the peaks of mass 290.5-291.5 (upper graph), of the peak of mass 285.5-286.5 (middle graph) and of the total abundance of these two peaks (bottom graph). These results are obtained by on-line detection of the analyte solution that has previously flowed (without recycling) throughout the chamber of the electrophoretic separation device (chemical buffering system: IPG gel with the pH range 6-6.15 in contact with the analyte solution; applied electrical potential: 300 V, pumping rate 1 mL/min)

Figure 9:
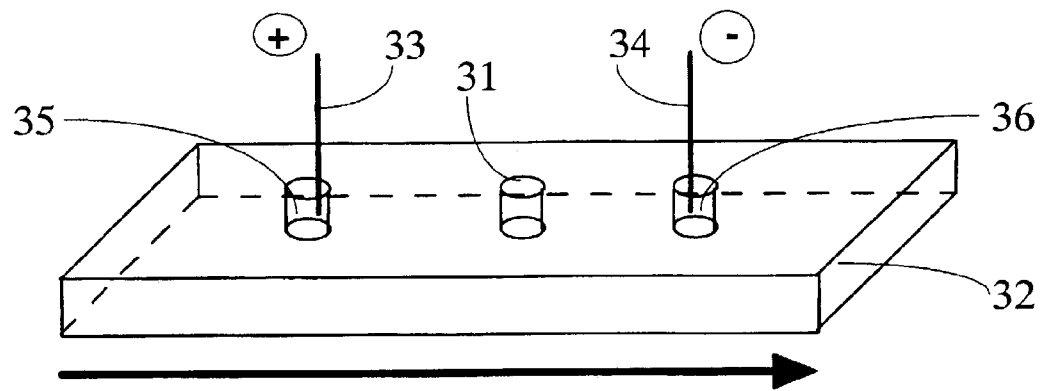

FIG. 9. Schematic representation of the set-up used for the electrophoretic separation in a static mode in a device where the inlet and outlet ends are merged, so that the chamber 31 is used as a reservoir in which the analyte solution can be introduced before purification and retrieved after purification. The analyte solution is only in contact with the chemical buffering system 32, and the electrical potential is applied through the anode 33 and the cathode 34 that are introduced in two reservoirs 35 and 36. The black arrow indicates the direction of the pH gradient introduced in the chemical buffering system.

Figure 10:
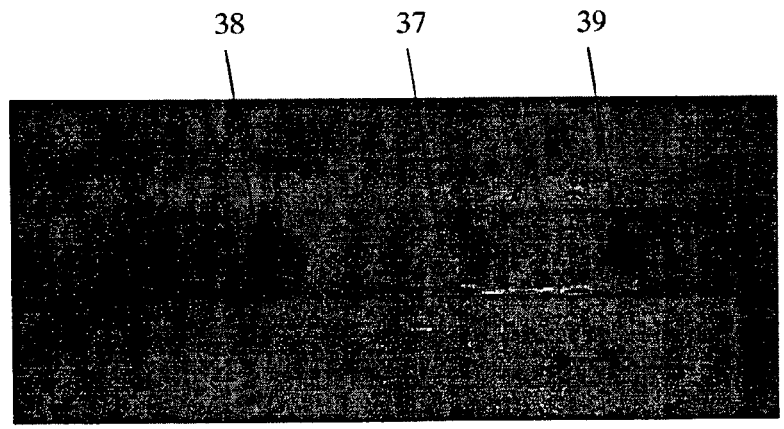

FIG. 10. Photograph of an IPG gel after purification of a 300 mM methylene blue and 10 mM phenol red water solution using a device similar to that of FIG. 9 and subsequent determination of the migrated methylene blue (spot number 39) and phenol red (spot number 38) to the cathodic and anodic reservoirs, respectively. The figure also shows that no colour is present after electrophoretic separation in the portion 37 of the gel that was in contact with the analyte solution during the purification.

Figure 11:
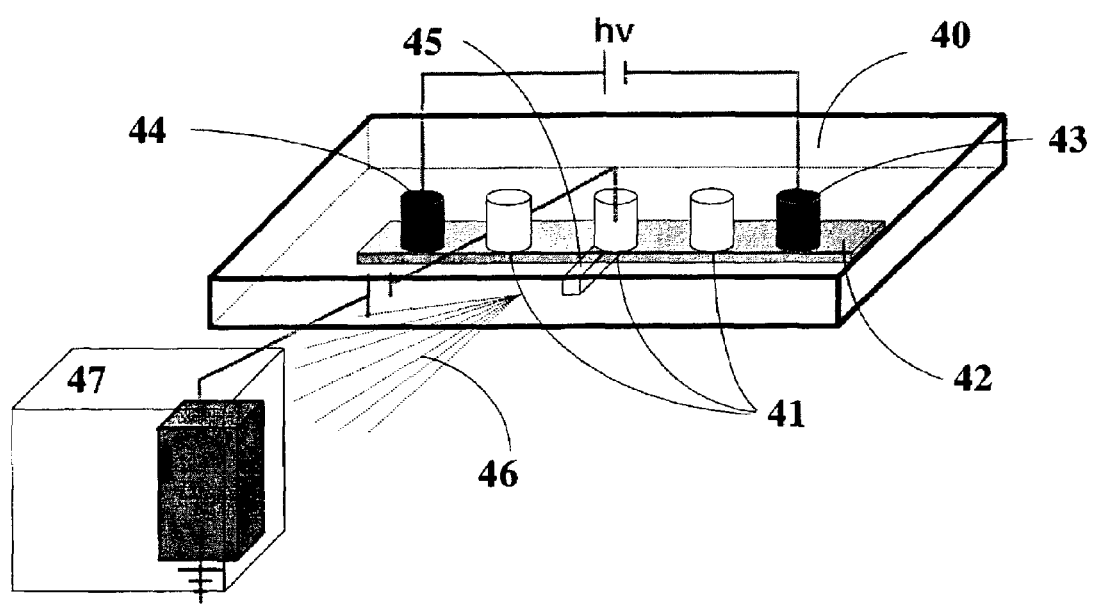

FIG. 11. Schematic representation of the set-up that can be used for the electrophoretic separation in a static mode with on-line detection using for example an electrospray mass spectrometer. In this example, the device is supported in a plastic support 40 containing the chamber 41 in contact with the chemical buffering system 42. The chamber is made of a series of three subchambers 40 in which the inlet and outlet ends are merged, so that said subchambers are used as reservoirs in which the analyte solution can be introduced before purification. Two supplementary reservoirs 43 and 44 are used to introduce the electrodes serving to apply the electrical field necessary for performing the electrophoretic purification. The subchambers also contain a supplementary connection system 45 (only one shown) for the coupling to another apparatus 47 serving as supplementary separation step or as a detector. The figure shows that an electrical potential can be applied between the subchambers (or a given position in the connection system) and the entrance of the apparatus 47 in order to control the hydrodynamic flow of the purified solutions and/or to generate an electrospray 46, thereby allowing to detect the compounds of interest present in the purified analytical solution.

DETAILED DESCRIPTION

EXAMPLE 1

Figure 1:
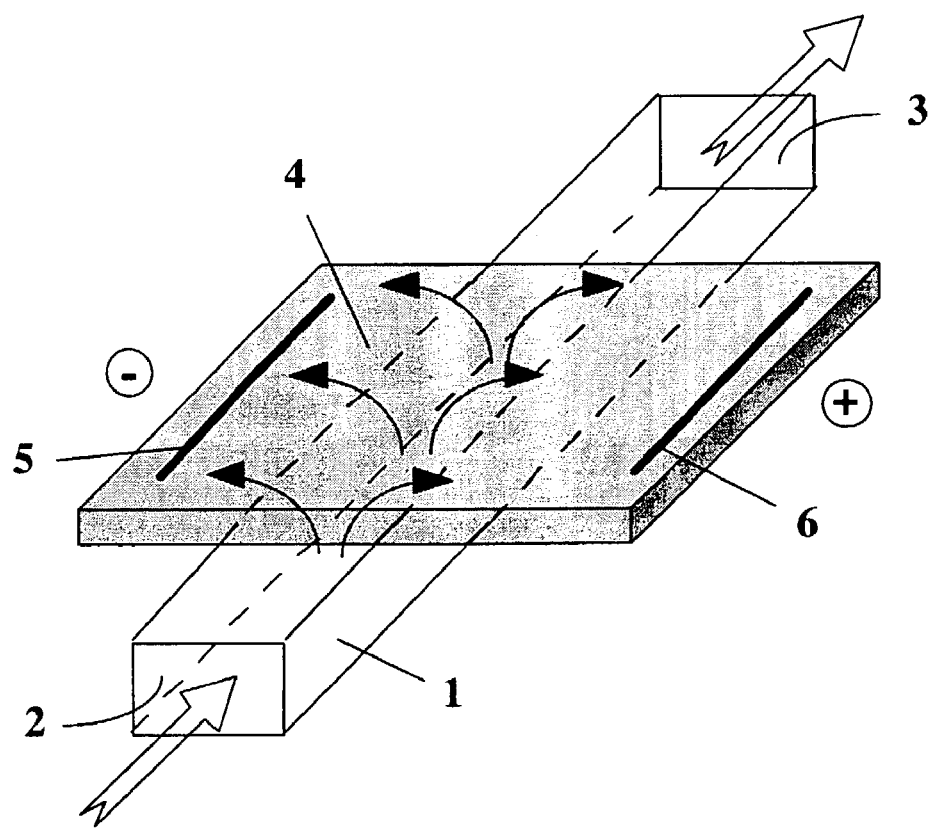
FIG. 1. Schematic representation of a separation device illustrating the purification concept. The chamber 1 containing the solution to purify has one inlet 2 and one outlet 3, located at opposite extremities and it is covered by the chemical buffering system 4. The cathode 5 and the anode 6 are placed parallel to the chamber and are only in contact with the chemical buffering system. The black arrows indicate the penetration of positively (versus cathode) or negatively (versus anode) charged compounds into the chemical buffering system, whereas the white arrows indicate that a flow of solution can be induced in the chamber.

Numerical Simulation of the Distribution of Migration Current within the Device of the Invention In order to understand the distribution of the migration current in the device of the present invention, a numerical simulation can be run with a finite element calculation. Such experiments allow one to predict the current flow through the purification device. To this end, FIG. 1 shows a schematic representation of an example of separation device and illustrates the purification concept. In this example, the device consists of a chamber 1 containing the solution to purify with one inlet 2 and one outlet 3 at each extremity of the chamber, of a chemical buffering system 4 in contact with a portion of the chamber and of two electrodes (a cathode 5 and an anode 6) that are only in contact with the chemical buffering system and placed parallel to the chamber. The black arrows indicate the penetration of positively (versus cathode) or negatively (versus anode) charged compounds into the chemical buffering system upon application of an electrical field between the two electrodes, whereas the white arrows indicate that a flow of solution can be induced in the chamber.

A cross section of the device, composed of a chemical buffering system as the cover of a channel is simulated, and the migration current is calculated in each point of the section. Two different cases have for example been simulated in the device where (i) the conductivity σ is identical in the gel and in the solution (σgel=σ solution) and (ii) the conductivity in the gel is ten times lower than in the solution (10 σgel=σsolution). For both cases, a calculation is solved in each point of the structure following the Laplace equation:

$$\nabla(-\sigma \nabla U) = 0 \tag{1}$$

and using the appropriate conditions in a two-dimensional system:
at the first electrode: U=0,
at the second electrode: U=1,
at the insulating wall:

$$\left(\frac{\partial U}{\partial N}\right)_{wall} = 0 \tag{2}$$

where U is the potential (V) and σ is the electrical conductivity ($.^{-1}m^{-1}$).

A stationary algorithm is used for the potential distribution. The simulations can be run using a commercial finite element software, Flux Expert® (Simulog, France) operating on a Unix workstation (Silicon Graphics Indigo 2 Solid Impact 10000 with 640 Mb RAM).

These simulation experiments aim at indicating whether the charged compounds migrate into the chemical buffering system or not, and at demonstrating the influence of the conductivity σ on the migration or in other words, the effect of the buffer composition in the solution to purify. The obtained results are presented in FIG. 2.

In the first case (FIG. 2A), σ is considered to be equal in the chemical buffering system and in the analyte solution (σgel=σsolution). A potential difference is applied between the two electrodes, which allows the prediction of the potential distribution. FIG. 2AI shows that the potential distribution in the solution corresponding to the segment under the gel is closely similar to that in the chemical buffering system. A potential gradient is also created in the chemical buffering system, which can lead to a pre-migration of proteins in the solution depending on their charge. As shown in FIG. 2AII, the current vectors indicate that the current is also transported through the solution. The vectors are similar in the middle of the structure and lead to an equal current flow. At the interface between the chemical buffering system and the solution, it is clearly demonstrated that a current flow takes place from the solution to the chemical buffering system.

In the second case (FIG. 2B), the conductivity of the solution is enhanced. It is considered 10 times higher in the analyte solution than in the gel (10 σgel=σsolution). The result of this experiment is that the potential gradient in the solution is less effective (see FIG. 2BIII), but that more current is transported in the solution than in the chemical buffering system (see FIG. 2BIV). It can also be demonstrated, as in the first case, that a current flow takes place from the solution to the chemical buffering system which enables the proteins to enter the chemical buffering system from the solution by migration.

From these two experiments, the concept of the separation and purification device of the present invention may be demonstrated. Even if the potential is only applied to the chemical buffering system, the analyte solution adjacent to it is affected by this potential, and a migration of charged compounds (for example proteins) is induced. The two cases differ only in their effectiveness. In the second case, a higher conductivity is considered, corresponding to, for example, a buffered protein solution. This is certainly more desirable for the protein stability and if the charge of some proteins have to be pre-selected for an isoelectric separation experiment. On the other hand, it is clear that the first case favours protein migration and therefore also the effectiveness of the purification device as nearly 100% of the current is carried by proteins in, for example, a non-buffered solution (sample diluted in water).

EXAMPLE 2

Electrophoretic Separation and Purification in a Non-Buffered Solution

In order to demonstrate the electrophoretic separation and purification of various solutions, the following experimental conditions have been employed:

Reagents

IEF protein marker standard is obtainable from BioRad (Herkules, US). Equine cytochrome c, B-lactoglobuline A and B, trypsin inhibitor and equine myoglobin can be purchased from Sigma. Immobiline DryPlates pH range (4.5-5.4 and 4-7, 11 cm) are obtainable from Pharmacia Amersham. The reagents for capillary isoelectric focusing (CIEF) are all obtainable from BioRad.

Experimental Setup

Figure 2:
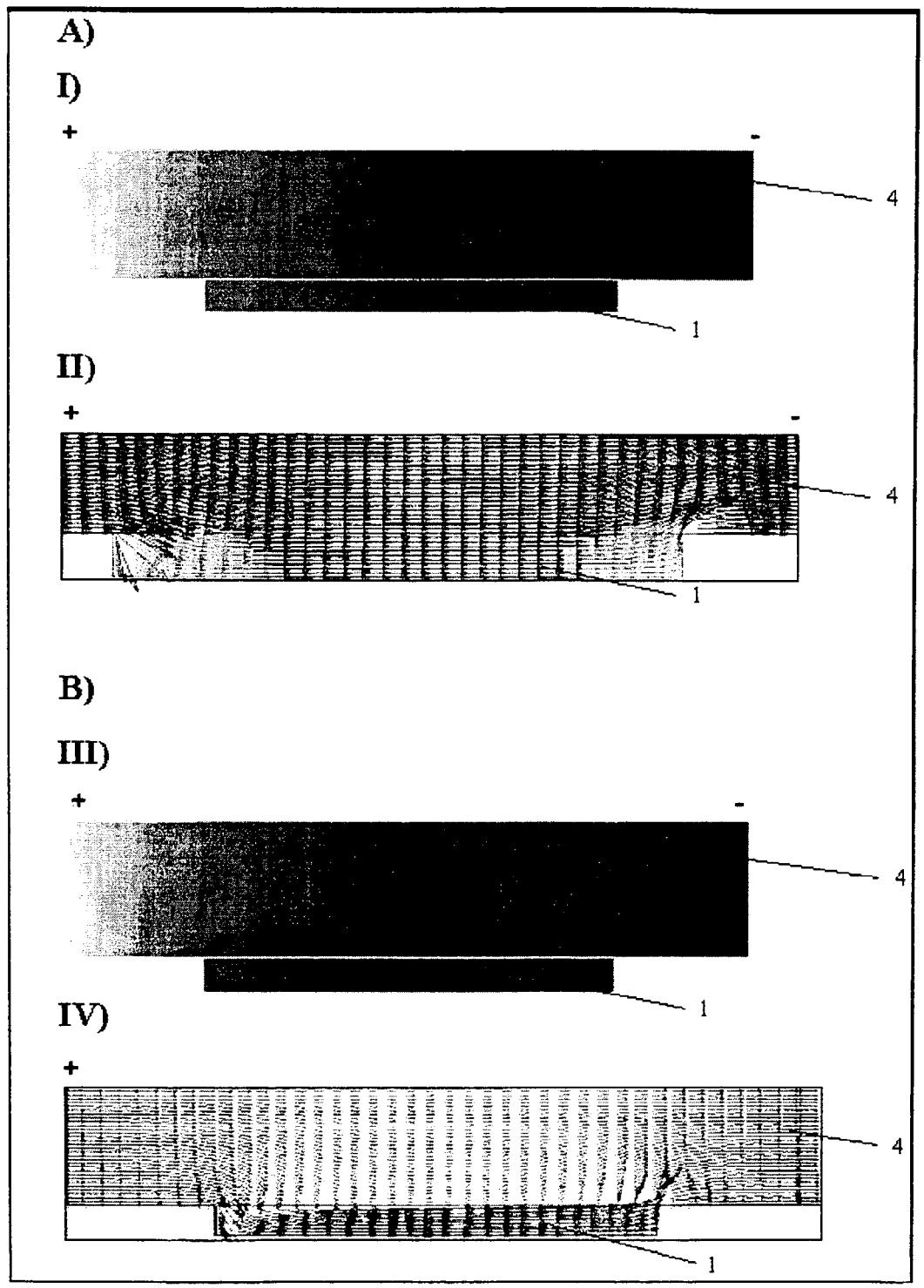
FIG. 2. Simulation results for an electric field applied to a gel matrix and its effects on the solution for two values of the gel and solution conductivity σ.

A plastic holder can be constructed in such a manner that the solution to purify can be pumped through the device containing the chamber contacting the chemical buffering system (which is an immobiline gel in the present case). FIG. 2 shows a photograph of a prototype of separation and purification device that has such an arrangement. The chamber 1 possesses one inlet 2 and one outlet 3 that are connected to teflon tubes and a peristaltic pump (not shown) in order to let the analyte solution flow through the device. The chemical buffering system 4 is an immobilised pH gradient (IPG) gel placed above the chamber. The entire device is held in a screwed plastic support 8, and its watertightness is ensured by an o-ring 7 which allows a tight seal. The cathode 5 and the anode 6 are placed in contact only with the IPG gel, close to the o-ring. These electrodes are made of thin platinum wires, so that they can be integrated above the o-ring without generating any leakage in the device. When the gel re-swells in the device, it encloses the electrodes completely and prevents the analyte solution from touching the electrodes. Re-swelling of the gels can be achieved for 1 h up to overnight in water or in the buffer system in which the purification experiment can be carried out.

Purification

The different protein solutions (1 ml total volume) can be applied to the device using the peristaltic pump. Before the experiment, the solution can be circulated for at least 2 min, and a sample of 100 µl can be taken for CIEF. A constant voltage varying from 30-100 V according to the experiment can then be applied using a high voltage power supply (Spellmann, CZE1000, New York, US). Voltage and current can be recorded with a LabVIEW 5 program operated on a Digital PC and a data acquisition board (Lab PC+, National Instruments, US).

Capillary Isoelectric Focusing (CIEF)

A Biofocus 3000 apparatus (BioRad, Hercules, US) can be used for CIEF analysis using BioCap XL coated capillaries (ID 50 µm, BioRad). The protein samples can be diluted in ampholytes (Bio-Lyte, BioRad) and analysed using BioRad IEF catholyte, anolyte and mobiliser. When necessary the samples can be ultracentrifugated with Biomax 5 kDa filters (Millipore, Bedford, Mass., US) prior to dilution in ampholytes, in order to guarantee sufficient concentration of proteins for the CIEF analysis.

Photography

Digital photographs of the dried immobiline gels and the device after the experiments can be taken with a digital camera (Fuji MX-700, Fuji Photo Film, Tokio, Japan) and treated with Adobe Photoshop software.

EXAMPLE 2.1

Separation of Protein Markers at pH 7

In order to demonstrate protein migration as predicted in the simulation of the first case of Example 1 where the gel and solution have identical conductivity, an immobiline gel of a pH range between 6.9-7.1 can be integrated in a prototype of device as claimed by the present invention (see FIG. 3).

TABLE 1

Proteins in the IEF marker standard solution from BioRad and their corresponding pI and colour.

| Protein | isoelectric point | colour |
|---|---|---|
| Phycocyanin | 4.6 | blue |
| beta-lactoglobuline B | 5.1 | — |
| bovine carbonic anhydrase | 6.0 | — |
| human carbonic anhydrase | 6.5 | — |
| equine myoglobin | 7.0 | brown |
| human haemoglobin A | 7.1 | red |
| human haemoglobin C | 7.5 | red |
| lentil lectin III | 7.8 | — |
| lentil lectin II | 8.0 | — |
| lentil lectin I | 8.2 | — |
| Cytochrome c | 9.6 | brown |

A solution of protein IEF markers in water (concentration of approx. 150 mg/ml, protein composition see Table 1) can be applied and continuously circulated through the device of FIG. 3 using a peristaltic pump at a constant pump rate (0.6 ml/min). A photograph of the immobiline gel after 1 hour purification upon application of an electrical potential of 100 V is shown in FIG. 4. For this experiment, the portion of the IPG gel in contact with the analyte solution has a pH of 7±0.14. This figure shows a blue band 9, indicating the migration of the blue coloured protein phycocyanin towards the anode and a brown band 10, indicating cytochrome c, myoglobin and haemoglobin migrating towards the cathode.

The proteins are concentrated in bands which demonstrate an electrophoretic focalisation mechanism. This clearly indicates that protein migration is induced from the solution to the gel, although the electrical potential is applied from electrodes only in contact with the gel. This also empirically confirms that the above simulation data agree with the experiment.

EXAMPLE 2.2

Purification of beta-Lactoglobuline B and Phycocyanin from a IEF Marker Solution In a further experiment, the purification of a solution consisting of the IEF marker proteins of Table 1 is demonstrated with a gel of pH range 4-5.5 with the pH gradient parallel to the Platinum electrodes. A CIEF analysis is carried out before and after the purification experiment (pump rate 0.6 ml/min, constant voltage=50 V). As presented in FIG. 5, the comparison of the two electropherograms demonstrates that the proteins of the original analyte solution with pI values higher than 5.5 migrated into the gel, whereas beta-lactoglobuline B and phycocyanin (peaks 11 and 12) are still contained in the solution after electrophoretic purification.

A simple comparison can also be carried out by eye. The solution before the experiment is green (colour of the complex solution of IEF markers) whereas the solution is blue after the purification (corresponding to the colour of phycocyanin). Additionally, the gel only exhibits a brown colour at the cathode side, corresponding to the positively charged proteins migrating towards it.

This experiment demonstrates that an analyte solution containing compounds of interest can be purified by extraction of charged compounds using a device and method of the present invention.

EXAMPLE 2.3

Purification of beta-Laglobulines A and B

A protein solution consisting of five proteins with known isoelectric points (trypsin inhibitor (pI=4.6), beta-lactoglobulin A (pI=5.3), beta-lactoglobulin B (pI=5.2), equine myoglobin (pI=7.0), cytochrome c (pI=9.6), at a concentration of 200 µg/ml except trypsin inhibitor with 50 µg/ml in water) is applied to the device of FIG. 3 containing an immobiline gel of a pH range from 5 to 5.4, rehydrated in water. As illustrated in the scheme of the separation process of FIG. 6B, the aim of this experiment is to recover beta-lactoglobulines A and B in solution. To this aim, the purification is based on the following principle: proteins with 5.0<pI<5.4 are either charged negatively in the gel near the cathode and repelled (pH in gel>pI), as illustrated by the proteins of type A in FIG. 6B. On the other more acidic gel extremity near the anode, these proteins of type A are positively charged (pH in gel<pI) and again repelled. In this manner, they cannot be extracted from the analyte solution. All other proteins with pI>5.4 are positively charged and attracted to the cathode (proteins of type B in FIG. 6B), whereas all proteins with pI<5.0 are attracted by the anode (proteins of type C in FIG. 6B). These last two types of compounds are thus extracted into the IPG gel upon electrophoretic purification of the analyte solution.

The electropherograms of the solution of the five above proteins are examined before and after purification and the results reported in FIG. 6AI and II show that the proteins trypsin inhibitor, equine myoglobin and equine cytochrome c disappeared nearly totally after purification, whereas the two beta-lactoglobulins stay in the solution. This is a clear proof for the purification principle based on isoelectric separation according to the present invention.

One advantage of the device as claimed in this invention is that the proteins to be purified are in minimal contact to the immobiline matrix, which reduces possible effect the polyacrylamide matrix could have on the proteins. They can be recovered easily in solution for further analysis. No extraction with chemicals needs to be carried out, minimising the effect of chemicals to the protein of interest. This fact also reduces the purification time. We could show here that the purification of microgram quantities can be carried out in 1 h. It may even be enhanced with the use of a cooling device or a different geometry ensuring less current flow through the device. This would allow the application of a higher electrical potential.

EXAMPLE 3

Electrophoretic Separation in a Buffered Solution

To test the simulation of the second case of the simulation experiment of example 1 where the conductivity of the gel is ten times lower that the solution, the solution of the protein markers of Table 1 is adjusted to a given pH. An acetate buffer (0.01 M) with a pH of 4.6 is used for this purpose. This pH corresponds to the pI of phycocyanin which is contained in the IEF marker standard (see Table 1). The pH range of the gel varied between 4.5-4.58 and 4.58-4.66. In these experiments, the current is set constant to 300 µA, which is the upper limit of the power supply. The voltage that has been detected to never exceed 30 V. After several hours of electrical potential application, only very little protein is visible in the gel (results not shown). These proteins are very diffuse and not focused in a band as in the above experiments. Also, bubble formation is enhanced, thereby causing a certain destruction of the gel in the device.

These experiments clearly show that the migration efficiency of the proteins is dramatically decreased if the sample solution is buffered. It is clear that more current is carried by buffering ions, when their concentration is high in comparison to that of the protein mixture. On the contrary, the current is mainly transported by the proteins themselves when they are contained in water only. This favours protein migration and therefore the separation efficiency of the device. While water is not the most favoured analyte solvent for proteins, the above method does not need any addition of buffer ions or ampholytes for the enhancement of isoelectric separation. In a practical point of view, this greatly facilitates the separation process.

EXAMPLE 4

Electrophoretic Purification Coupled with On-Line Mass Spectrometry Detection

A device similar to that shown in FIG. 3 can be coupled to a mass spectrometer (LCQ-DUO, Finnigan) for on-line detection of the compound or compounds of interest. To this aim, a mixture of 80 µM catechine and 20 µM methylene blue can be pumped through the electrophoretic separation device at a rate of 1 mL/min (using a peristaltic pump from Ismatec). The device contains a chemical buffering system made of an IPG gel of pH 5.5 to 6.5, so that the portion of the gel in contact with the chamber exhibits the pH range 6-6.15. The outlet end of the chamber is connected by tubings to the injection system of a LCQ-DUO mass spectrometer for on-line analysis of the solution.

Catechine is a well-known mass marker that is neutral between pH 6 and 6.15, whereas methylene blue is a permanent cation. When this mixture flows in the device of the present invention, methylene blue is extracted out of the analyte solution and penetrates into the IPG gel upon application of an electrical potential (for example 300 V). In this manner, methylene blue is eliminated from the solution, and the catechine is purified. This is evidenced in FIGS. 7 and 8 that show the mass spectrogram of the analyte solution before and, respectively, after electrophoretic purification. To this end, the results of FIG. 7 have been obtained with 1 µL of the starting analyte solution that has been electrosprayed from a syringe in the mass spectrometer (in atmospheric pressure chemical ionisation (APCI) mode, with nitrogen as sheath gas and with the following working conditions: voltage source: 3.82 kV; current source: 5.4 mA; vaporizer temperature: 450° C.; sheath gas flow rate: 79.9 psi; capillary voltage: 4.6 V and capillary temperature: 200° C.). The obtained spectrum mainly shows two very strong peaks at the mass/charge (m/z) ratios of 286.3 and 291 corresponding to methylene blue and catechine, respectively. The intensity of the peak at m/z=291 is only about 60% that of the peak at m/z=286.3, in agreement with the larger concentration of methylene blue in the analyte solution. After electrophoretic purification of the analyte solution, the mass spectrum of FIG. 8 exhibits a similar shape, but the relative abundance of the peaks become almost the same (the intensity of the peak at m/z=291 is 94% that of the peak at m/z=286.3). The experiment can be run further, and the evolution of the relative abundance of the two peaks with time shows that the intensity of the peak at m/z=291 remains approximately constant, whereas that of the peak at m/z=286.3 passes from 100% to less than 40% within less than two minutes.

These results clearly indicate that the analyte solution has been purified, in agreement with the blue band of methylene blue observed in the gel close to the cathode. The length of the chamber (about 3 cm) is not sufficient to completely eliminate methylene blue from the analyte solution, but the dimension of the chamber, the flow rate of the analytical solution as well as the value of the electrical field can be optimised to allow complete purification.

This experiment clearly demonstrates that the device of the present invention can be coupled to a mass spectrometer for on-line detection of the purified solution. In this manner, further separation or detection of the purified solution can be easily conducted. In some applications, the purified fractions can also be collected in another support before further analysis, like for instance a MALDI (matrix assisted laser desorption ionisation) plate.

EXAMPLE 5

Electrophoretic Purification of Isoforms

In order to demonstrate the separation and purification of protein isoforms, N-acetyl Eglin C is obtainable by recombinant DNA techniques containing two isoforms (one in basic pH and one in acid pH range).

A water solution of 1 mg/mL N-acetyl Eglin C can be recycled in the device of the present invention and run constantly at 1000 volts for 1 hour on an immobilsed pH gradient gel at pH 5.5 (pI of N-acetyl Eglin C).

The results that can be obtained using a conventional capillary isoelectric focusing apparatus (Biofocus, Bio-Rad) show that the analyte solution to purify presents one peak after 26.86 min. (corresponding to the basic isoform pI 6.2: 4.86%), a main peak after 29.56 min. (corresponding to Eglin C: 90.18%) and a peak after 31.52 min. (corresponding to the acid isoform pI 5.2: 4.94%). After separation and purification according to the method of the present invention, the purified solution shows a very small peak corresponding to a trace of basic isoform at 26.38 min. And a peak at 29.57 min. (97.88%) corresponding to the main component of N-acetyl Eglin C. No peak corresponding to the acid isoform is present, demonstrating the isoform separation and purification and the enrichment of the main component.

EXAMPLE 6

Electrophoretic Purification in Static Mode

For certain applications, it may be advantageous to purify the analyte solution without hydraulic flow. In such cases, the device of the present invention does not require a chamber with inlet and outlet ends, but only a reservoir to introduce the analyte solution and retrieve it.

This is exemplified in FIG. 9 which shows a schematic representation of the set-up used for the electrophoretic separation in a static mode in a device where the inlet and outlet ends are merged, so that the chamber 31 is used as a reservoir in which the analyte solution can be introduced before purification and retrieved after purification. The analyte solution is only in contact with the chemical buffering system 32, and the electrical potential is applied through the anode 33 and the cathode 34 that are introduced in two reservoirs 35 and 36. The black arrow indicates the direction of the pH gradient introduced in the chemical buffering system.

For the demonstration of the separation with such a device of the present invention, one can fabricate an electrophoretic separation device similar to that shown in FIG. 9 which includes an immobilised pH gradient (IPG) gel serving as chemical buffering system and a chamber containing three sub-chambers consisting of small plastic tubes that are placed on the top of the IPG gel and disposed along the direction of the pH gradient. As schematically illustrated in FIG. 9, the analyte solution can be introduced into the central subchamber, whereas the two other subchambers are filled with water and contain each an electrode so as to serve as cathodic and anodic reservoirs, respectively. In this manner, the electrodes are not directly in contact with the analyte solution. The electrical field has to pass through the IPG gel, and a portion of the electric field penetrates into the subchamber containing the analyte solution to purify.

To demonstrate the separation and purification of an analyte solution with such a configuration of electrophoretic device, an immobiline gel (pH range 4-7) can be reswelled in water overnight at room temperature. Three plastic wells (1 cm diameter) with holes (0.8 cm in diameter) opened in their bottom can be placed on top of the IPG gel, respectively on the pH 4.5, pH 5.5 and pH 6 lines. One hundred µL of a 300 µM methylene blue and 10 mM phenol red water solution can then be deposited in the central well in contact with the gel at pH 6. Two platinum electrodes can be respectively placed in the right and left side wells which are filled with water.

In these conditions, both compounds are charged over the whole pH range imposed by the IPG gel, since methylene blue is a permanent cation and phenol red is negatively charged below its pKa which has a value of 7.81. Methylene blue exhibits a blue colour whereas phenol red is yellow in its anionic form, so that extraction of both analytes out of the analyte subchamber into the IPG gel upon application of an electrical potential can be easily identified. Indeed, upon application of a constant voltage (500 V) between the two platinum electrodes using a high voltage power supply (Landis & Gyr), it can be seen that methylene blue migrates towards the cathode, whereas phenol red migrates towards the anode. After one hour of purification, a digital photograph of the gel is taken with a numerical camera (Camedia C-2020 Z—Olympus) and treated with Olympus Camedia software. This photograph of the IPG gel presented in FIG. 10 shows that the purification is complete, which is demonstrated by the fact that the central reservoir is colourless (absence of colour in the portion 37 of the gel that was in contact with the analyte reservoir), whereas the portion of the gel below the anodic reservoir is yellow (spot 39 in FIG. 10) and that below the cathodic reservoir is blue (spot 39 in FIG. 10).

These results clearly demonstrate the efficiency of the method of the present invention, even when no flow is induced to the analyte solution to purify. However, agitation may be induced either to the subchambers or to the entire device, so as to increase the convection. As the efficiency and rate of the separation depends on the migration of the charged compound in the analyte solution, it may be advantageous to avoid the formation of concentration gradients and hence to insure homogeneity of the analyte solution. For certain applications like protein purification, it can also be advantageous to control the temperature of the subchambers and to add means of avoiding precipitation (for example by sonicating the subchambers).

It is worth noting here that the solutions in the anodic and cathodic reservoirs can be slightly coloured at the end of the purification. In such a case, this indicates that part of the methylene blue and part of the phenol red are extracted out of the IPG gel into the anodic and, respectively, the cathodic reservoirs, thereby allowing to recover in solution the compounds that have been extracted from the analyte solution into the chemical buffering system. This can be useful in many applications and demonstrates one interest of disposing a plurality of sub-chambers in the separation device so as to collect various purified fractions, as specified in some embodiments of the present invention.

An example of purification device containing a plurality of subchambers is shown in FIG. 11 which is a schematic representation of the set-up that can be used for the electrophoretic separation in a static mode with on-line detection or connection to a further separation step. In this illustration, the device is supported in a plastic support 40 containing the chamber 41 in contact with the chemical buffering system 42. The chamber is made of a series of subchambers 41 in which the inlet and outlet ends are merged, so that said subchamber are used as reservoirs in which the analyte solution can be introduced before purification and retrieved after purification. Only three subchambers are represented here, but there is no limitation in the number, disposition and shape of these subchambers. Two supplementary reservoirs 43 and 44 are used to introduce the electrodes serving to apply the electrical field necessary for performing the electrophoretic purification. The subchambers also contain a supplementary connection system 45 (only one shown) for the coupling to another apparatus 47 serving as supplementary separation step or as a detector. The figure shows that an electrical potential can be applied between the subchambers (or a given position in the connection system) and the entrance of the apparatus 47 in order to control the hydrodynamic flow of the purified solutions and/or to generate an electrospray 46, thereby permitting detection of the compounds of interest present in the purified analytical solution.

Finally, recovery of the compound or compounds of interest in solution greatly facilitates further separation, purification and/or detection. To this end, the subchambers of the devices described in the present experiment can contain a connection (like for example an aperture, a groove, a sealed tube, a capillary, a sealed micro-channel or any other coupling system) that allows on-line introduction or injection of the purified solution into another detection system (see FIG. 11 for an example). Such a system can be demonstrated with a conventional liquid chromatograph that is used for example to further separate a cellular extract that has been purified by the electrophoretic method of the present invention and that contains several compounds of interest that need to be identified individually. Similarly, the subchambers of the present device can for example be directly coupled to a mass spectrometer (with direct sampling using aspiration, mechanical or electrokinetic pumping), thereby allowing on-line identification of the compound or compounds of interest.

All publications and patent applications cited in this specification are herein incorporated by reference. Although the foregoing invention has been described in some detail by way of illustration and examples for clarity of understanding, it will be readily apparent to a person skilled in the art in light of the teachings of this invention that certain changes and modifications may be made thereto without departing from the spirit or scope of the appended claims.

The invention claimed is:

1. A device for electrophoretic separation and purification of charged and neutral compounds in an analyte solution, said device comprising:

(a) a chamber containing said analyte solution, at least a part of one wall of the chamber being composed of the buffering face of a first portion of a chemical buffering system, said chemical buffering system defining a desired pH or pH gradient in said first portion contacting said analyte solution, said first portion being integral with a remaining portion of said chemical buffering system extending outside of said chamber, said first portion enabling the charged compounds to migrate from said analyte solution in said chamber into said remaining portion of said chemical buffering system and out of said chamber while the neutral compound and said analyte solution remain within said chamber; and (b) means for producing a potential difference across said chemical buffering system to generate an electric field that is distributed along said buffering face of said chemical buffering system and that penetrates into said analyte solution in said chamber at a position of said first portion of said chemical buffering system in contact with said analyte solution, whereby compounds that are globally neutral at said pH or pH range defined by said first portion of said chemical buffering system contacting said analyte solution remain in said chamber upon potential application, whereas compounds that are charged at said pH or pH range defined by said first portion of said chemical buffering system contacting said analyte solution migrate and are extracted out of said chamber into said chemical buffering system upon potential application.

2. A device according to claim 1 wherein said chamber has an inlet and an outlet connected to a hydraulic flow system, wherein the analyte solution is capable of flowing through said chamber.

3. A device according to claim 1 wherein the chamber constitutes a reservoir in which the analyte solution can be introduced before separation and purification and from which the purified solution can be retrieved.

4. A device according to claim 1, wherein the desired pH or the pH gradient in said chemical buffering system is produced using covalently linked buffering molecules.

5. A device according to claim 1, wherein said chamber has an inlet and a plurality of outlets, thereby allowing the collection of fractions at different portions of the chemical buffering system.

6. A device according to claim 1, wherein said chamber has a plurality of sub-chambers, said sub-chambers being interconnected by said chemical buffering system, thereby defining a desired pH value or a desired pH gradient in each sub-chamber.

7. A device according to claim 1, wherein said means for producing said potential difference along said chemical buffering system comprises electrodes.

8. A device according to claim 1, wherein said chemical buffering system is capable of isoelectric separation of at least one compound of interest at a defined pH value or in a defined pH range.

9. A device according to claim 1, wherein said chemical buffering system defines in said first portion contacting said analyte solution in said chamber a pH gradient of less than 0.1 pH unit.

10. A device according to claim 1, wherein said chemical buffering system contains means for direct identification or quantification of one of a compound and a class of compounds that have been extracted from the analyte solution out of the chamber.

11. A device according to claim 10, wherein said identification and/or quantification means is based on the production of light, the absorption of light, the reaction with a blotting agent or label, the generation of an electroactive species or the specific molecular recognition of compounds.

12. A device according to claim 1, further comprising a fine membrane separator that stops direct adsorption of the neutral compounds onto the chemical buffering system wall.

13. A device according to claim 1, further comprising means to control the temperature of said device and the analyte solution.

14. A device according to claim 1, further comprising coupling means permitting purified analyte solution or recovered charged compounds to be passed from the device into other separation or detection systems.

15. A device according to claim 1, wherein said device is multiplexed to perform one of simultaneous and parallel electrophoretic separation and purification of charged and neutral compounds.

16. A device according to claim 1, wherein said chemical buffering system is selected from a group consisting of a gel comprising immobilised buffering molecules and a buffering fluid solidified in one of a polymer matrix, a fritted glass, a porous membrane, a filter and a combination thereof.

17. A device according to claim 1, further comprising means for collecting separated fractions in an ampholyte-free or buffer-free solution.

18. A device according to claim 1, further comprising means to recycle separated fractions in said chamber.

19. A device according to claim 1, further comprising means to pump said analyte solution in said chamber.

20. A device according to claim 19, wherein a direction of the electrical field is substantially perpendicular to a direction of a flow of the analyte solution within the chamber.

21. A device according to claim 1, wherein a length of said chamber is substantially perpendicular to a direction of the pH gradient of the chemical buffering system and to a direction of the electric field.

22. A device according to claim 1, further comprising electrodes that are in contact with said chemical buffering system on opposite sides of said chamber a spaced distance from said chamber so as not to be in direct contact with the analyte solution.

23. A device according to claim 1, wherein said means for producing said potential difference along said chemical buffering system comprises electrodes integrated within the chemical buffering system.

24. A method of electrophoretic separation and purification of charged and neutral compounds in an analyte solution and collection of separated fractions comprising the steps of:
   (a) providing a device comprising:
      (i) a chamber containing said analyte solution, at least a part of one wall of the chamber being composed of the buffering face of a first portion of a chemical buffering system, said chemical buffering system defining a desired pH or pH gradient in the first portion contacting said analyte solution, the first portion being integral with a remaining portion of said chemical buffering system extending outside of the chamber, the first portion enabling the charged compounds to migrate from said analyte solution in the chamber into the remaining portion of said chemical buffering system and out of the chamber while the neutral compound and said analyte solution remain within the chamber; and
      (ii) electrodes adapted to generate an electric field that is distributed along said buffering face of said chemical buffering system and that penetrates into said analyte solution in the chamber at a position of the first portion of the chemical buffering system in contact with the analyte solution,
   (b) applying a potential difference between said electrodes so that compounds that are globally neutral at the pH or pH range defined by the first portion of the chemical buffering system contacting the analyte solution remain in the chamber upon potential application, whereas compounds that are charged at the pH or pH range defined by the first portion of the chemical buffering system contacting the analyte solution migrate and are extracted out of the chamber into said chemical buffering system.

25. A method according to claim 24, wherein the compounds are biological compounds, organic compounds, proteins or protein derivatives, or isoforms.

26. A method according to claim 24, wherein the analyte solution is one of a non-aqueous solution and a solution containing an organic solvent.

27. A method according to claim 24, wherein the device is used to load the chemical buffering system with compounds of interest.

28. A method according to claim 27, wherein the analyte solution is renewed in the chamber in order to accumulate compounds of interest in the chemical buffering system.

29. A method according to claim 24, further comprising the step of recycling the analyte solution and the separated fractions in said chamber.

30. A method according to claim 24, further comprising the step of recovering the separated fractions in solution.

31. A method according to claim 30, wherein the separated fractions are recoverable in one of an ampholyte-free solution and a buffer-free solution.

32. A method according to claim 24, further comprising the step of pumping the analyte solution through said chamber during the separation.

33. A method according to claim 24, wherein a direction of the pH gradient of the chemical buffering system and a direction of the electric field is substantially perpendicular to a length of the chamber.

34. A kit comprising a device and instructions for electrophoretic separation and purification of charged and neutral compounds in an analyte solution, said device comprising a chamber for containing the analyte solution and a chemical buffering system arranged in such a manner that:
   (a) at least a part of one wall of the chamber is composed of the buffering face of a first portion of said chemical buffering system, said chemical buffering system defining a desired pH or pH gradient in said first portion in contact with said analyte solution, said first portion being integral with a remaining portion of said chemical buffering system extending outside of said chamber, said first portion enabling the charged compounds to migrate from said analyte solution into said remaining portion of said chemical buffering system and out of said chamber while the neutral compound and said analyte solution remain within said chamber;
   (b) said device having means for producing a potential difference across said chemical buffering system to generate an electric field that is distributed along said buffering face of said chemical buffering system and that penetrates into said analyte solution within said chamber at the position of the first portion of the chemical buffering system in contact with the analyte solution, whereby compounds that are globally neutral at the pH or pH range defined by the first portion of the chemical buffering system contacting the analyte solution remain in said chamber upon potential application, whereas compounds that are charged at the pH or pH range defined by the first portion of the chemical buffering system contacting the analyte solution migrate and are extracted out of the chamber into said chemical buffering system upon potential application.

35. A kit according to claim 34, wherein said compounds that are globally neutral at the pH or pH range defined by the portion of the chemical buffering system contacting the analyte solution are recoverable in an ampholyte-free or buffer-free solution.

36. A kit according to claim 34, further comprising specific chemicals that are necessary to mix with the analyte solution for the electrophoretic separation and purification.

37. A kit according to claim 34, further comprising at least one of specific chemicals and a separation system that is necessary to prepare the analyte solution before the electrophoretic separation and purification.

38. A kit according to claim 37, wherein said separation system is one of a cut-off membrane and a desalting system.

39. A kit according to claim 34, wherein said chemical buffering system is selected from a group consisting of a gel comprising immobilised buffering molecules and a buffering fluid solidified in one of a polymer matrix, a fritted glass, a porous membrane, a filter and a combination thereof.

40. A kit according to claim 34, wherein a length of said chamber is substantially perpendicular to a direction of the pH gradient of the chemical buffering system and to a direction of the electric field.

* * * * *

UNITED STATES PATENT AND TRADEMARK OFFICE
CERTIFICATE OF CORRECTION

PATENT NO. : 7,615,354 B2  
APPLICATION NO. : 10/275041  
DATED : November 10, 2009  
INVENTOR(S) : Faupel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2023 days.

Signed and Sealed this

Nineteenth Day of October, 2010

David J. Kappos  
*Director of the United States Patent and Trademark Office*